(12) United States Patent
Wade

(10) Patent No.: US 8,235,720 B2
(45) Date of Patent: *Aug. 7, 2012

(54) PROPHYLACTIC SYSTEMS FOR DENTAL INSTRUMENTS AND METHODS FOR USING THE SAME

(76) Inventor: Eric V. Wade, Tyler, TX (US)

(*) Notice: Subject to any disclaimer, the term of this patent is extended or adjusted under 35 U.S.C. 154(b) by 83 days.

This patent is subject to a terminal disclaimer.

(21) Appl. No.: 12/564,690

(22) Filed: Sep. 22, 2009

(65) Prior Publication Data

US 2010/0009309 A1   Jan. 14, 2010

Related U.S. Application Data

(60) Division of application No. 11/050,496, filed on Feb. 2, 2005, now Pat. No. 7,625,209, which is a continuation of application No. 10/068,626, filed on Feb. 5, 2002, now Pat. No. 6,948,934, which is a continuation of application No. 09/426,219, filed on Oct. 22, 1999, now Pat. No. 6,350,124.

(51) Int. Cl.
*A61C 1/16* (2006.01)
(52) U.S. Cl. ........................................ 433/116
(58) Field of Classification Search .......... 433/115, 433/116
See application file for complete search history.

(56) References Cited

U.S. PATENT DOCUMENTS

| 881,856 | A | | 3/1908 | Hagstrom | |
|---|---|---|---|---|---|
| 1,222,996 | A | | 4/1917 | Rhodes | |
| 1,539,253 | A | * | 5/1925 | Fuller | 433/116 |
| 1,742,061 | A | * | 12/1929 | Curry | 433/116 |
| 2,041,077 | A | * | 5/1936 | Lininger | 433/116 |
| 3,324,552 | A | | 6/1967 | Saffir | |
| 3,881,838 | A | | 5/1975 | Derbyshire | |
| 4,266,935 | A | * | 5/1981 | Hoppe | 433/116 |
| 4,424,036 | A | | 1/1984 | Lokken | |
| 4,693,871 | A | * | 9/1987 | Geller | 433/116 |
| 4,728,290 | A | * | 3/1988 | Eisner et al. | 433/116 |
| 5,078,605 | A | | 1/1992 | Sutter et al. | |
| 5,310,341 | A | | 5/1994 | Byer | |
| 5,380,201 | A | * | 1/1995 | Kawata | 433/132 |
| 5,490,781 | A | * | 2/1996 | Wade | 433/116 |
| 5,772,367 | A | | 6/1998 | Daniel | |
| 6,102,631 | A | | 8/2000 | Nyari | |
| 6,273,716 | B1 | | 8/2001 | Wade | |
| 6,350,124 | B1 | * | 2/2002 | Wade | 433/116 |
| 6,948,932 | B2 | | 9/2005 | Jung et al. | |
| 6,948,934 | B2 | * | 9/2005 | Wade | 433/116 |

* cited by examiner

*Primary Examiner* — Ralph Lewis
(74) *Attorney, Agent, or Firm* — Armstrong Teasdale LLP

(57) ABSTRACT

A prophylactic system 100 for a dental hand piece 101 of a selected shape and having an outlet 112 for providing a fluid to an operating field is disclosed. A cover 102 has a shape substantially similar to the hand piece 101 for enclosing the dental hand piece 101 and includes an aperture 118 for communicating with the operating field. An s-shaped valve 600 includes a path 605 for coupling the fluid from outlet 118 of the hand piece 101 to the aperture 118 of the cover.

17 Claims, 8 Drawing Sheets

PROPHYLACTIC SYSTEMS FOR DENTAL INSTRUMENTS AND METHODS FOR USING THE SAME

This application is a Divisional Application of application Ser. No. 11/050,496 filed Feb. 2, 2005, which is a Continuation Application of application Ser. No. 10/068,626 filed Feb. 5, 2002, now U.S. Pat. No. 6,948,934 which is a Continuation Application of application Ser. No. 09/426,219 filed Oct. 22, 1999, now U.S. Pat. No. 6,350,124.

BACKGROUND OF THE INVENTION

1. Field of the Invention

The present invention relates in general to dental instruments and in particular to a prophylactic system for dental instruments and methods for making the same.

2. Description of the Related Art

In recent years, the various health professions have come under close scrutiny due to the increased possibility of the transmission of infectious diseases from doctor to patient, patient to doctor, and patient to patient. This is particularly true in the dental office, where dental appliances come in direct contact with potentially harmful fluids or blood-born pathogens, such as Hepatitis B and HIV, found within the oral cavity. With the predicted increase in the number of cases of infection with the Hepatitis B and HIV viruses, dentists will be treating more patients carrying these infections, knowingly or unknowingly. Consequently, the possibility of accidental transmission of these dangerous infectious diseases will correspondingly increase.

One particular path of pathogen transmission within the dental office is through the high speed and low speed air-driven dental hand pieces. These appliances come in direct contact with the patient's oral cavity during use and often collect blood, minute debris and other microbial and particulate matter, which have been shown to be a source of blood-born pathogen transmission, including the transmission of the Hepatitis B and HIV viruses. Because of the potential for transmission of pathogens by dental hand pieces, the Occupational Safety and Health Administration has issued detailed guidelines for proper handling and sterilization of these devices following each patient use. Among other things, proper hand piece sterilization involves autoclaving the instrument at approximately 15 psi and 121° C. for a period of thirty minutes (cold sterilization using a disinfectant solution is often ineffective). This requirement, although necessary, drastically reduces the number of patients that can be effectively treated during the dentist's normal work day due to the increased time required to both autoclave and cool instruments. (The cost of dental hand pieces range from a few hundred to well over a thousand dollars, which makes it economically difficult to maintain a large number of such appliances in order to handle an increased patient load). Moreover, repetitive autoclaving has been shown to decrease the useful life of the instruments themselves.

Another concern related to the use of high-speed dental hand pieces is the noise level at which the dentist is exposed. The typical high-speed dental hand piece produces noise in the frequency range of 2,000 to 3,500 Hertz, with a typical amplitude of 80 decibels at approximately 2,000 Hertz. With the average dentist spending many hours per week, over a number of years, exposed to the noise from dental appliances, the potential readily exists for the dental practitioner to experience some type of hearing disorder.

In sum, the need has arisen for apparatus and methods which provide a practical means for preventing dental hand pieces from coming in direct contact with potentially harmful fluids or blood-born pathogens found within the oral cavity. Moreover, it would be highly advantageous if such methods and apparatus could also reduce the noise level to which the dental practitioner is exposed during the use of such hand pieces.

SUMMARY OF THE INVENTION

A prophylactic system is disclosed for a dental hand piece of a selected shape and having an outlet for providing a fluid to an operating field. A cover is provided having a shape substantially similar to a shape of the hand piece for enclosing the dental hand piece. The cover includes an aperture for communicating with the operating field. An s-shaped valve includes a path for coupling the fluid from outlet of the hand piece to the aperture of the cover.

The principles of the present invention are also embodied in a dental system which includes a hand piece, an inner cover, and an outer cover. The hand piece includes a burr and air and water outlets for performing dental operations in an oral operating field. The inner cover has a shape substantially conforming to a shape of the hand piece and encloses the hand piece. The inner cover includes a first aperture for receiving the burr and a second aperture for passing air and water from the air and water outlets of the hand piece. The outer cover has a shape substantially conforming to the shape of the inner cover and encloses the inner cover. The outer cover further includes a first aperture for receiving the burr and a second aperture for passing air and water passed from the inner cover to the operating field.

Methods are also disclosed for protecting a dental hand piece from exposure to potential hazardous materials during a dental procedure. One such method includes the step of enclosing the hand piece with an inner cover having a shape substantially conforming to a shape of the hand piece. The inner cover includes a first aperture for receiving a burr coupled to the hand piece and a second aperture for passing a fluid provided by an outlet on the hand piece. The method additionally includes the step of enclosing the inner cover with an outer cover, the outer cover including a first aperture for receiving the burr and the second aperture for passing the fluid output from the second aperture of the inner cover to a dental operating field.

Additionally, a burr assembly is disclosed for use with a dental hand piece. The assembly includes a dental burr and a splash guard coupled to the dental burr and having means for propelling liquids and debris away from the hand piece during rotation of the burr.

In sum, the principles of the present invention provide a practical means for preventing dental hand pieces from coming in direct contact with potentially harmful fluids or blood-born pathogens during dental procedures. Moreover, the double cover system substantially reduces the noise level to which the dental practitioner is exposed during such a procedure.

BRIEF DESCRIPTION OF THE DRAWINGS

For a more complete understanding of the present invention, and the advantages thereof, reference is now made to the following descriptions taken in conjunction with the accompanying drawings, in which.

DESCRIPTION OF THE PREFERRED EMBODIMENTS

The principles of the present invention and their advantages are best understood by referring to the illustrated embodiment depicted in FIGS. 1-7.
of the drawings, in which like numbers designate like parts.

Figure 1A:
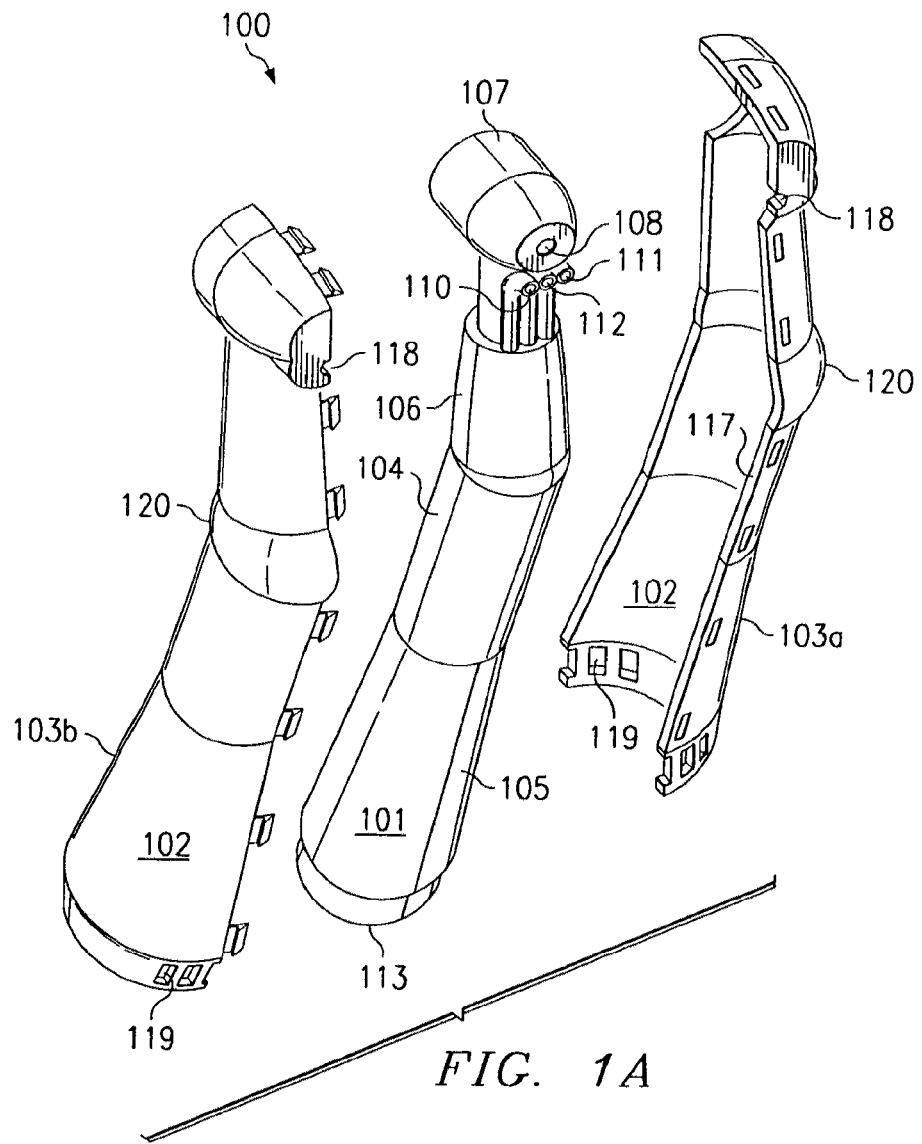
FIGS. 1A-1C depict a series of perspective views of the inner portions of a dental hand piece-cover system according to the principles of the present invention.
Figures 1B, 1C:
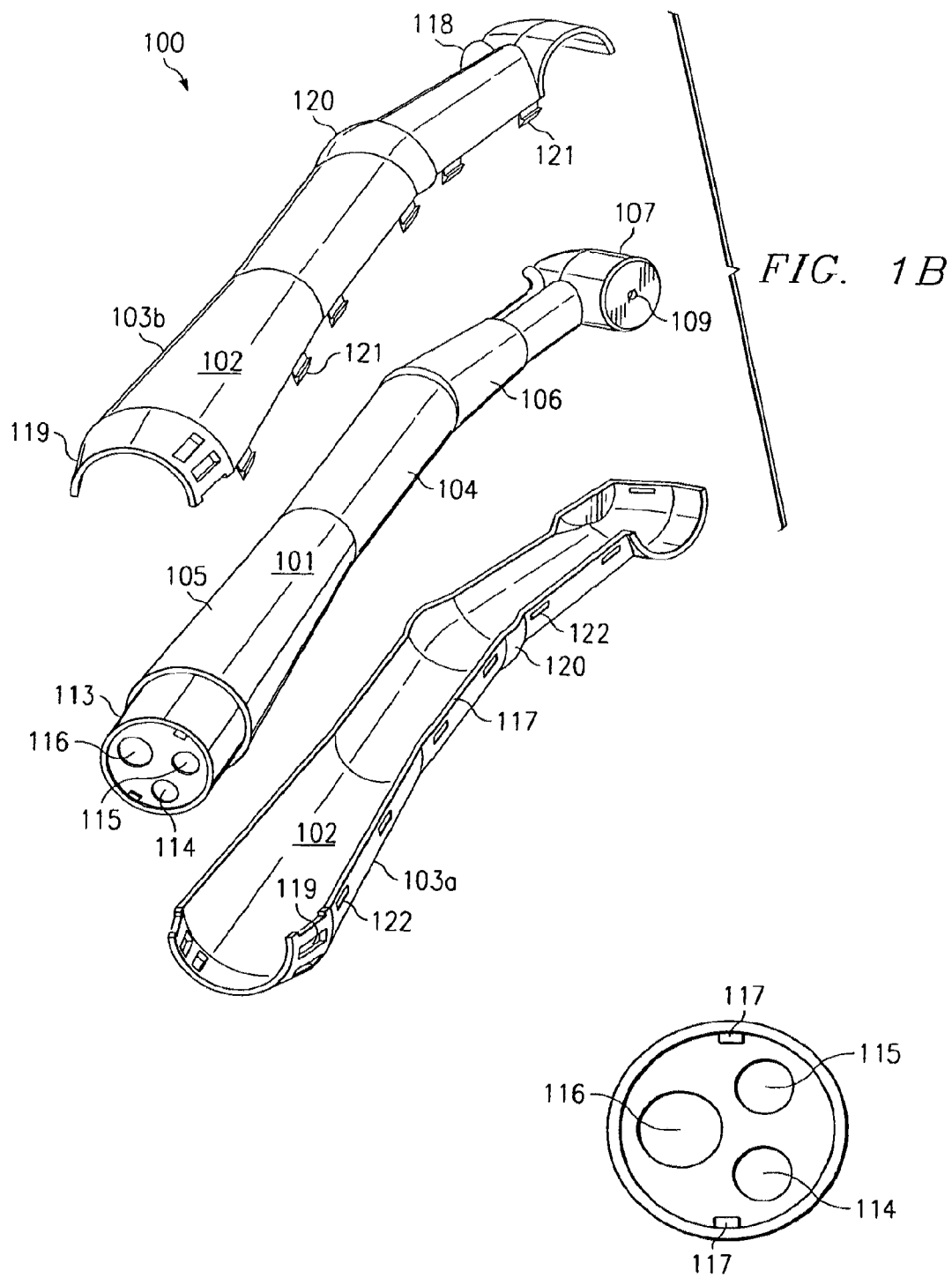

FIG. 1A-1C depict a series of perspective views of the inner portions of a dental hand piece-cover system 100 according to the principles of the present invention. The primary components depicted in these figures include a high-speed air-driven dental hand piece 101 and a first or inner cover 102 comprised of first and second interlocking halves 103a and 103b. The two halves 103 of inner cover 102 are mirror symmetric and generally have dimensions and shape adapted to receive and enclose hand piece 101. The primary portions of hand piece 101 are the main body 104, handle 105, neck 106, and head 107. Neck 106 is disposed at an angle to body 104 such that head 107 is disposed at a contra-angle to body 104 and handle 105.

Head 107 encloses an air-driven turbine which drives an interchangeable dental burr which is received through burr opening 108. A burr changing mechanism 109 is provided which is accessible through the rear of head 107. The burr may also be used by the use of socket-like opening which receive the burr changing tool used to both loosen and tighten the burr.

Located at the front of head 107, and immediately below burr receptacle 108 are air-supplied delivery tube and opening 111, and fiber optic light 112. Tubing within hand piece 101 carries water and pressurized air, at approximately 5-60 psi, from an adapter 113 to openings 110 and 111, respectively.

Figure 2:
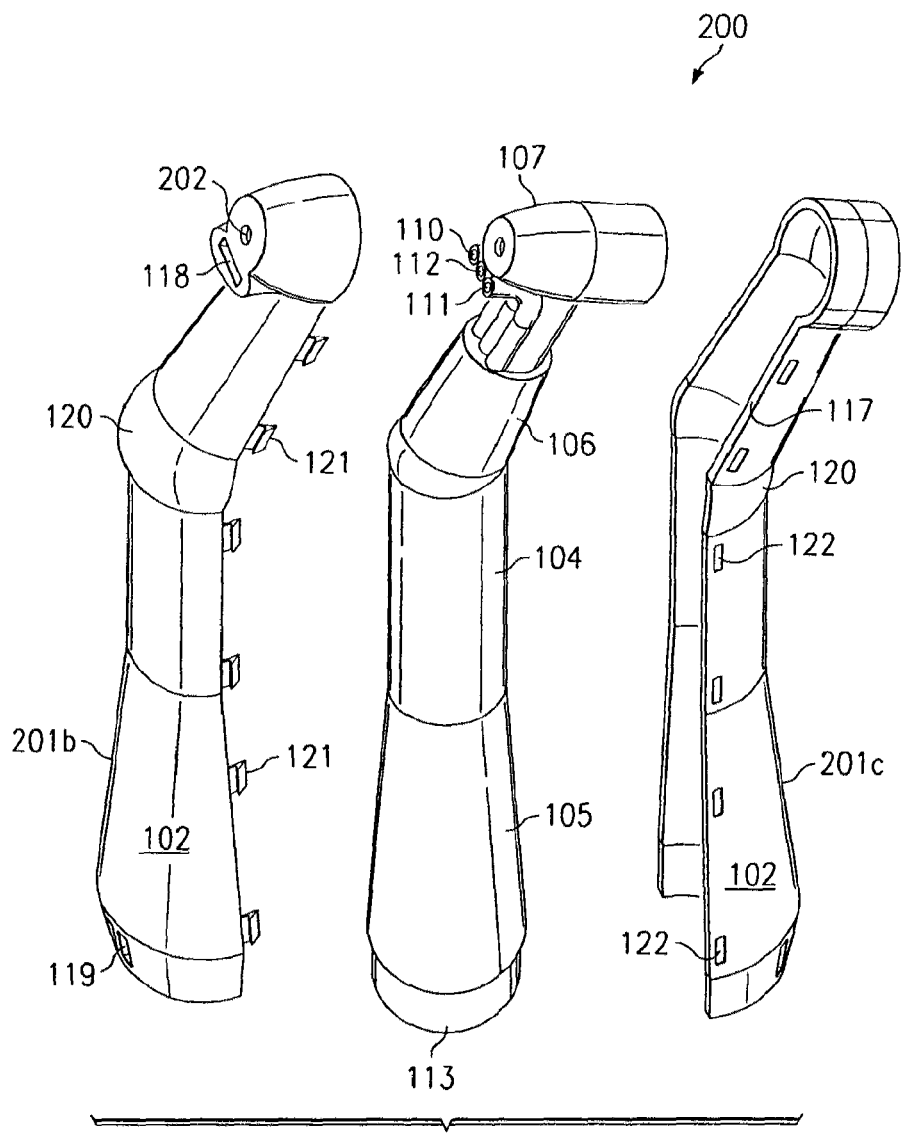
FIG. 2 depicts in detail and adapter, which connects to conventional dental water and air source.

Adapter 113, which connects to conventional dental water and air source, is shown in FIG. 1C, and in more particular detail in FIG. 2. Adapter 113, includes an aperture or receptacle 114 for introducing water, an aperture or receptacle 115 for receiving air, and a light cover 116 for transmitting light from a fibre optic light source to the head 107.

The two halves 103 of inner cover 102 are preferably constructed from a plastic ranging in thickness from 0.01 mm to 100 mm. Preferably, absorbent strips 44 are glued or otherwise fastened along the outer edges of halves 103. When corresponding edges of the two halve abut, therefor, a first (inner) seal is provided to prevent the ingress or egress of hazardous fluids and particles. Moreover, absorbent strips 117 may be pretreated or post-treated with a variety of substances, including anti-viral, antibacterial, antibiotic or disinfectant substances, to further improve the barrier against the transmission of hazardous materials. When half covers 103a and 103b are assembled to form inner cover 102, an aperture 118 is defined which allows light from light source 112 and water form water aperture 111 to reach the dental operating field. Specifically, aperture 118 acts as a one-way flow valve which protects from the uptake of hazardous fluid and debris into the confines of inner cover 102. Specifically, exit aperture 118 is wide enough to allow for the excess of air and water under pressure of the air compressor, but narrow enough to resist the intake of fluid and other materials. The surface tension of the fluid, as well as capillary action of the reduced size.

Apertures 119 are provided at the connector end of inner cover 102, in conjunction with similar apertures through the outer cover, allow for the dissipation of compressed air used to drive the air turbine in head 107. A soft insert 119, made of rubber or similar material, may be included for damping vibration and noise.

FIG. 2 is an alternate embodiment of the cover 102. In this case, the two halves 201 of cover 102, are formed with a 90° rotation with respect the halves 103 of the embodiment of FIGS. 1A and 1B.

FIG. 2 additionally shows another very important feature according to the principles of the present invention. Specifically, a circumferential or cone shaped burr opening cover 202 is provided through half 201b of inner cover 102. A cone shaped burr opening is adapted to receive the burr tool while aiding in the prevention of leakage of harmful materials and fluids into inner cover 102.

In the illustrated embodiments, the two halves of inner cover 102 are held together with a friction lock closure comprising an interlocking series of male tabs 121 and corresponding female apertures 122. Each male tab 121 includes a raised elevation or notch which captures the sidewall of the corresponding aperture 122. Tabs 121 are preferably formed integral with the corresponding half 103b or 201b of inner cover 102 and may have a thickness of between 0.01 mm to 10 mm and a width from 0.01 mm to 50 mm. The sidewalls of apertures 122 may be shaped or angled to improve interlocking with tabs 121.

Figure 3:
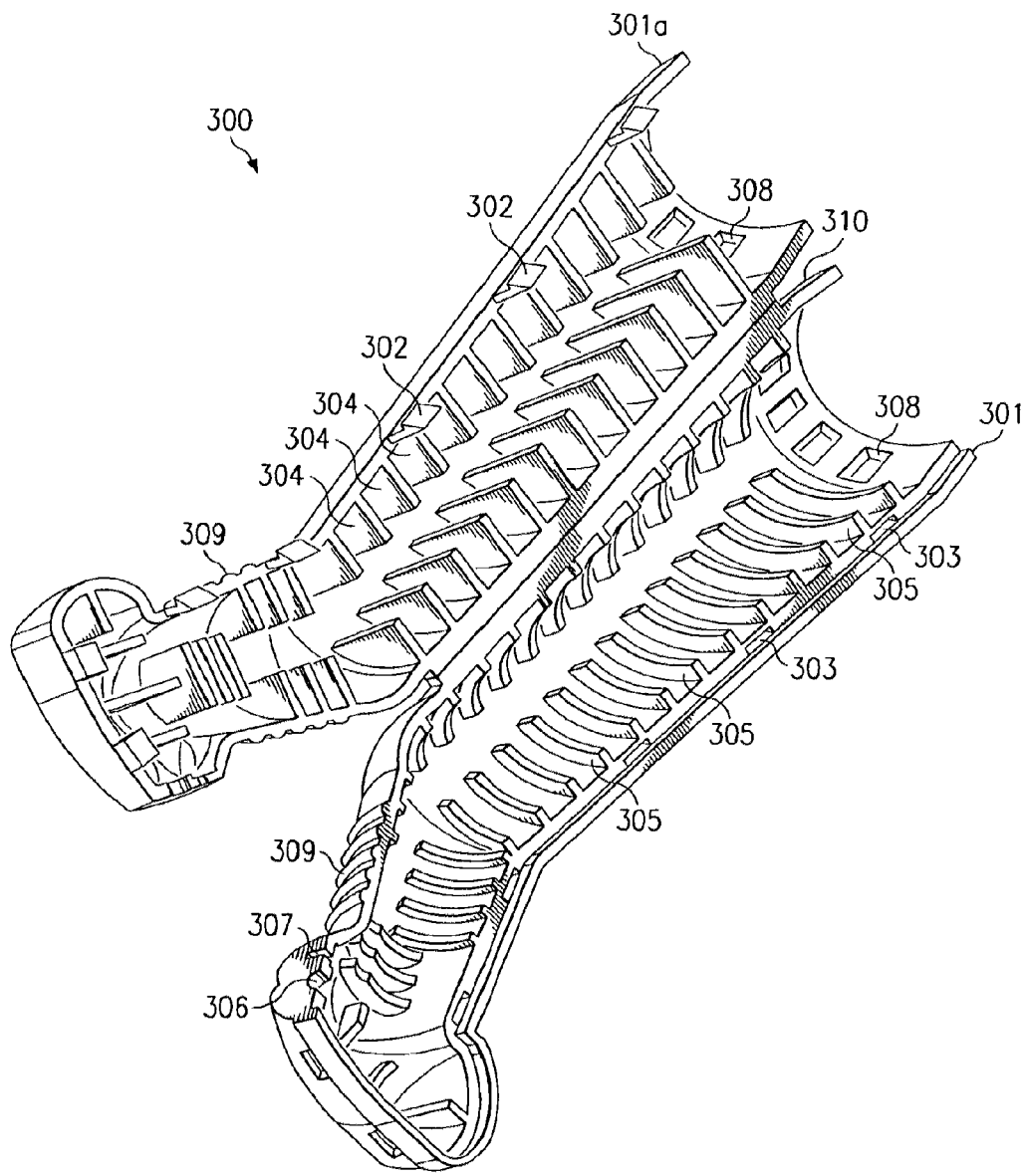
FIG. 3 is a schematic diagram of an outer cover according to the principles of the present invention.

FIG. 3 is a schematic diagram of an outer cover 300 according to the principles of the present invention. As with inner cover 102, outer cover 300 is preferably formed of injected molded and/or thermoformed plastic, although other materials such as rubber may also be used. FIG. 3 depicts outer cover 300 in an open configuration ready to receive the assembly comprised of hand piece 101 and inner cover 102. As with the inner cover, outer cover 300 includes two symmetric halves 301a and 301b. A hinge mechanism 310, for example, a thin layer of plastic formed integrally with the two halves 301 of cover 300, allows body halve 301 to rotate with respect to each other to thereby close outer cover 300. Cover 300 is held in the closed position using a friction lock mechanism including male tabs 302 and female apertures 303 on opposing edges of the corresponding halves 301. As described above with regards to inner cover 102, male tabs 302 include a raised protrusion or notch suitable for interlocking with the sidewalls of apertures 303. The sidewalls of apertures 303 may also be shaped or angled to improve the capture of tabs 302.

A plurality of treated antibiotic, anti-viral or disinfectant treated strips 304 and 305 are disposed along the length of respective half bodies 301a and 301b. Strips 304 are preferably made of compressed cotton, but other similarly absorbent materials may also be used. They may be treated, for example with a commercially available compound such as amoxicillin. In the illustrated embodiment, strips 304 are angled and strips 305 curved such that the inner cover/dental hand piece assembly 100 fits snugly within the confines of outer cover 300. In addition to providing a barrier against the ingress and egress of hazardous fluids and debris, strips 304 and 305 provide a series of mechanical absorbers and baffles which help produce the noise experienced by the dental practitioner as well as the patient.

An aperture or receptacle 306 is formed around the dental burr extending from hand piece 101. An additional aperture 307, directly below aperture 306, is formed allowing air, and/or light from source tubes 110-111 to reach the operating field. Additionally, apertures 308 are provided at the receptacle end of cover 300 for venting compressed air exhausted from the air turbine driving the burr.

Figure 4:
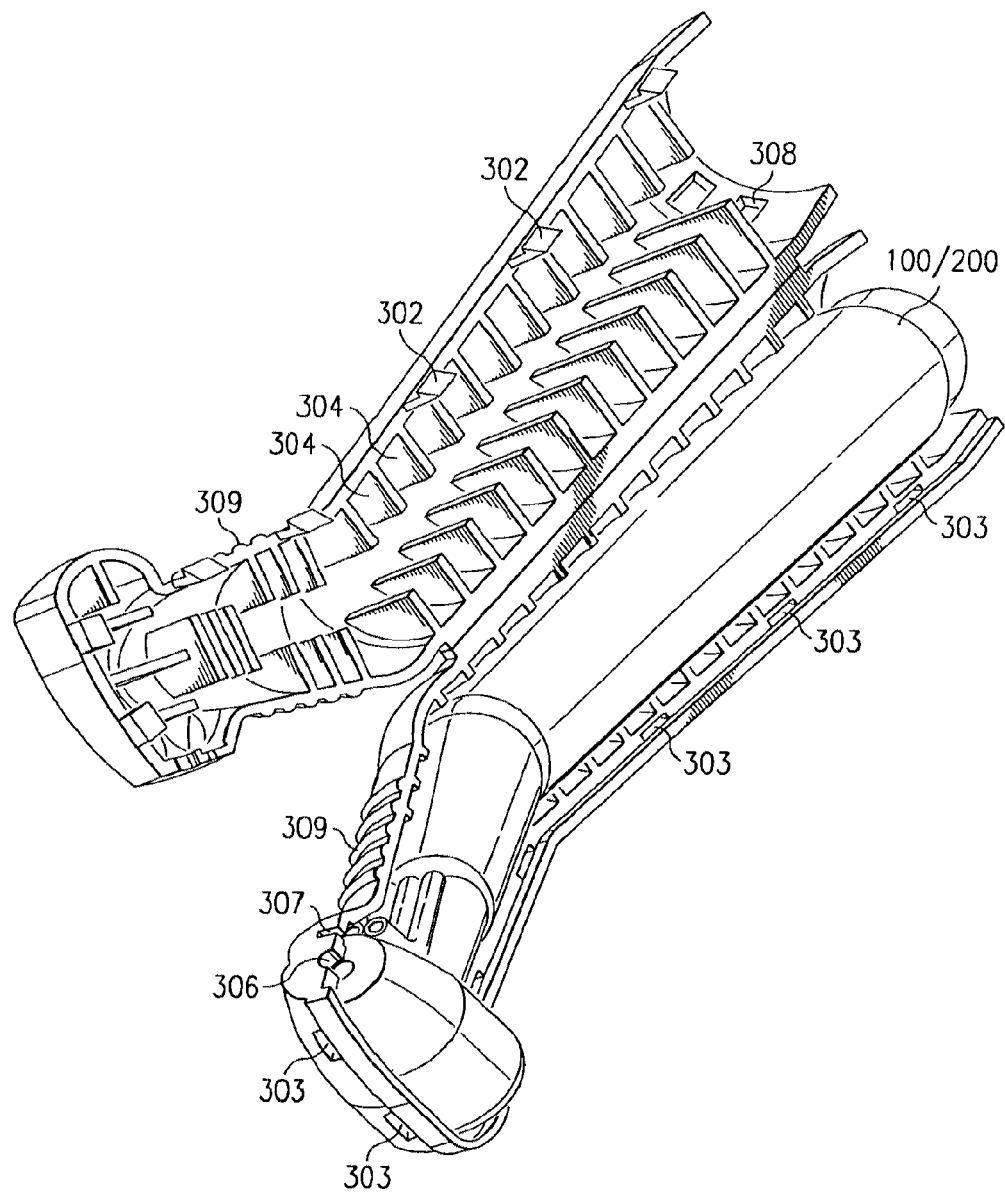
FIG. 4 is a diagram depicting a dental hand piece/inner cover assembly according to either embodiment, as received by outer cover.
Figure 5:
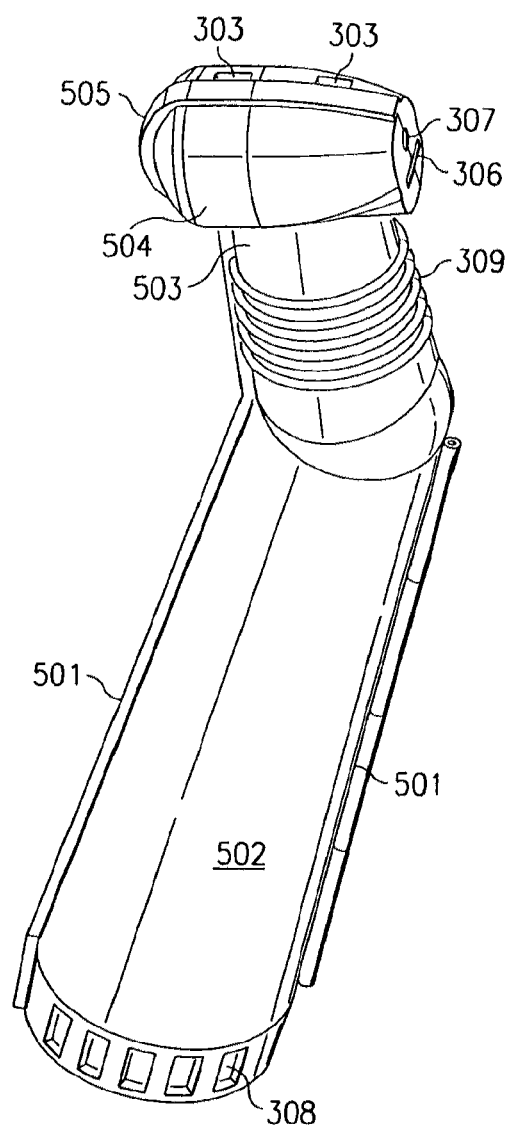
FIG. 5 provides an enclosed view of a dental hand piece/inner cover assembly, as received by outer cover.

FIG. 4 is a diagram depicting a dental hand piece/inner cover assembly according to either embodiment 100 or embodiment 200, as received by outer cover 300. In FIG. 4, the two halves of outer cover 300 have yet to be folded and locked together to complete the outer enclosure of the assembly. An enclosed view is provided in FIG. 5.

Figure 6B:
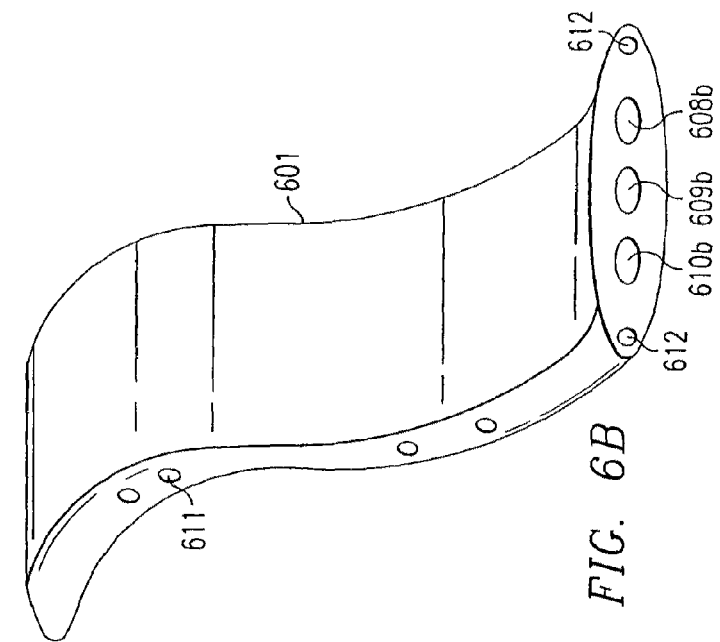
FIGS. 6A and 6B are respective front and rear views of a protective valve suitable for passing air, water and light from corresponding outlets of the hand to an aperture through the inner cover.
Figure 6A:
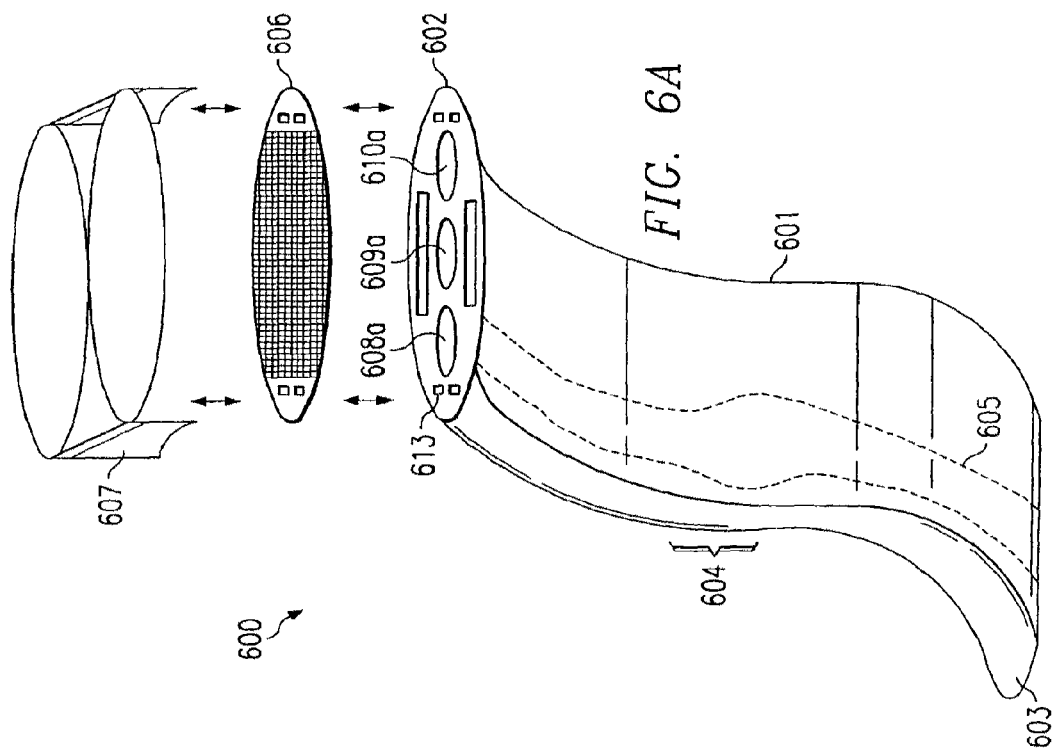

FIGS. 6A and 6B are respectively front and rear views of a preferred protective valve 600 for connecting water outlet 110, air outlet 112 and light source 112 of hand piece 101 with aperture 118 of inner cover 102. Valve includes a body 601, enclosing tubes and a fiber optic filament for transmitting the air, water and light received at hand piece interface 603 to inner cover interface 602.

Body 601 is formed of a rigid or semi-rigid material, such as metal, plastic or rubber, which allows body 601 to maintain a "backwards S-shaped" shape. This shape advantageously traps biological contaminants and debris which may be found in backwash and spray from the surgical field. In particular, such contaminants and debris are generally trapped in region 604 immediately above the point where the slope of the S-shaped curve reverses.

The enclosed water path 605 is represented in FIG. 6A by dashed lines. In region 604, the water path widens laterally and becomes thin vertically. This feature adds additional protection against the ingress of debris and contaminants towards the hand piece outlets, which are particularly susceptible retain contamination. A similar shape may also be used for the air path, which is not shown in the figures for brevity and clarity.

A mesh or filter 606 is provided at inner cover interface 602. Filter 606 may, for example, be made of an absorbent material, such as compressed cotton, which is impregnated with an anti-biological contamination agent, such as amoxicillin. A cover 607 is included for use when air or water is not being transmitted from the hand piece. Cover 607 preferably swivels between closed and open positions with respect to body 601 and may be spring-loaded such that it automatically returns to the closed position (covering inner cover interface 602) whenever pressurized air or water is not flowing outwards towards inner cover aperture 118.

Apertures 608a, 609a and 610a align and communicate with air outlet 112, water outlet 110 and light filament 112 of hand piece 101 and corresponding apertures 608b, 609b and 620b align and communicate with aperture 118 through inner cover 102. A series of apertures 611 may optionally be provided through the sides of valve body 601 for expelling contaminants and debris, which may have accumulated in the air and or water paths, under the pressure of the flowing air or water itself.

Valve 600 preferably couples to inner cover 102 and hand piece 101 through a friction lock mechanism which includes at least one mail tab protrusion on one of the mating components and at least one corresponding female receptacle on the other component of the mating pair. A single friction lock mechanism 612 may be used as shown in FIG. 6B where a single protrusion or receptacle is provided one each side of the corresponding interface 602/603 or a double friction lock mechanism 613 which utilizes both a protrusion and a receptacle on each side of the given interface 602 or 603.

Figure 7A:
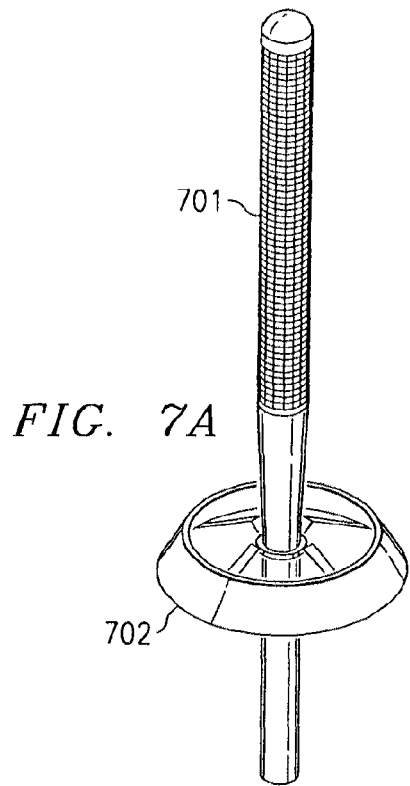
FIGS. 7A-7C are respective views of a bur-splash guard assembly, the bur apart from the assembly and the splash guard apart from the assembly.
Figure 7B:
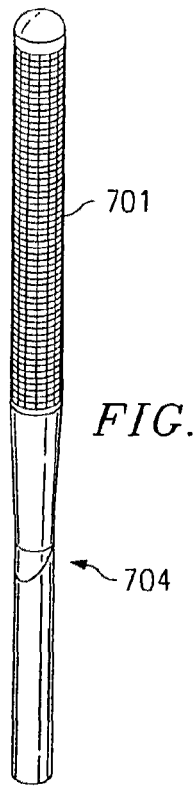
Figure 7C:
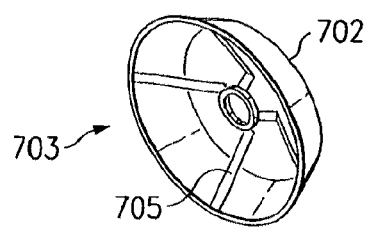

FIG. 7A is a diagram of a bur-splash guard 700 assembly embodying the principles of the present invention. Assembly 700 may be used with hand piece 101 alone or in combination with inner and outer covers 102 and 300. Assembly 700 includes a bur 701 and a splash guard 702. In addition to the view of the assembly provided in FIG. 7A, side view of bur 701 is provided in FIG. 7B and a front view of splash guard 702 is provided in FIG. 7C.

Splash guard 702 is secured to bur 701 by snapping the edge of inner aperture 703 of splash guard 702 into a V-shaped notch 704 on bur 701. In the secured configuration, splash guard 702 rotates along with bur 701. The inner face of splash guard includes a plurality of fins 705 which act similar to fan blades, Fins 705 force air, liquids and solid debris away from hand piece 101. In this fashion, an accumulation of debris around the bur end of hand piece 101 is minimized.

Figure 8:
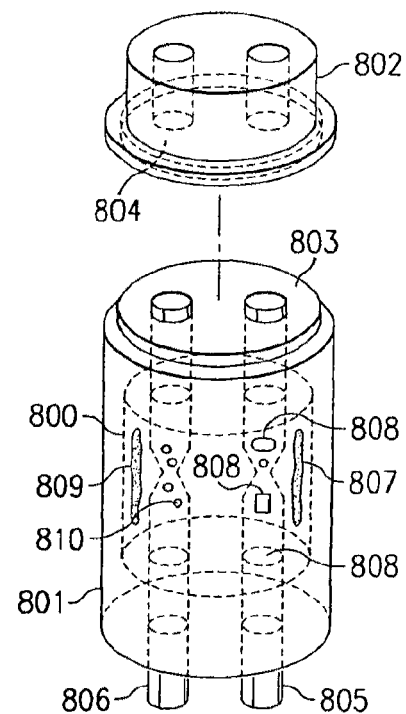
FIG. 8 is a cut-away view of an in-line air and water filter adapted for use with a dental hand piece, such as that shown in FIG. 1A, along with an adapter for coupling the filter and the hand piece when the filter is disposed external to the hand piece.

FIG. 8 is a cut-away view of an in-line air and water filter 800 which may provided internal to hand piece 101 or as part of an adapter coupling hand piece 101 with the practitioner's conventional source of compressed air and water. FIG. 8A shows the configuration where filter 800 is disposed within an adaptor 801 at the end of an air/water hose (not shown), along with an adapter 802 for coupling filter 800 with hand piece 101. Adapter 801 mates with adapter 802 with a friction lock mechanism including a male jack 803 on adapter 801 and a female receptacle 804 on adapter 802.

In the illustrated embodiment of filter 800, one water path 805 and one air path 806. In alternate embodiments, there may be multiple air and/or water paths, with the principles of the present applying equally as well. Water is filtered through an absorbent material 807, which may be compressed cotton strips or filaments impregnated with an anti-biotic or antiviral agent, such as amoxicillin. Preferably, material 807 is a filament type or mesh material with pores 808 which may be rectangular, circular or oval. Air passes through an absorbent material 809 such as preformed cotton, which has pores smaller or much smaller pores than the filament material of the water path, as is more appropriate for filtering a gas.

Although the invention has been described with reference to a specific embodiments, these descriptions are not meant to be construed in a limiting sense. Various modifications of the disclosed embodiments, as well as alternative embodiments of the invention will become apparent to persons skilled in the art upon reference to the description of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

It is therefore, contemplated that the claims will cover any such modifications or embodiments that fall within the true scope of the invention.

What is claimed:

1. A cover for a dental hand piece, said cover having a shape and dimensions selected to substantially surround the dental hand piece and conform with a shape and dimensions of the dental hand piece, said cover configured with a collared aperture to allow access to at least a bur receptacle of the dental hand piece, said cover further comprising:

a second aperture adjacent the collared aperture, said second aperture oriented to direct air and water from the dental hand piece toward an operating field of a bur positioned in the bur receptacle;

a filter fitted within said second aperture, said filter configured to filter air and water provided by the dental hand piece and routed through said second aperture for application to a patient; and a protective device for said filter, said protective device configured to cover said second aperture and said filter when the dental hand piece is not in use.

2. A cover according to claim 1 further configured to allow access to one or more openings in the dental hand piece which provide one or more of water and air at a pressure.

3. A cover according to claim 1 further configured to allow access to a light provided by the dental hand piece.

4. A cover according to claim 1 further configured to allow access to an adapter of the dental hand piece, the adapter configured to attach to one or more of a water source, an air source, and a light source.

5. A cover according to claim 1 further configured to allow access to a bur changing mechanism of the dental hand piece.

6. A cover according to claim 1, said cover comprising a plastic.

7. A cover according to claim 1 wherein said protective device is spring loaded.

8. A cover according to claim 1 wherein said filter is impregnated with an anti-biological contamination agent.

9. A cover for a dental hand piece, said cover having a shape and dimensions selected to substantially surround the dental hand piece and conform with a shape and dimensions of the dental hand piece, said cover comprising:

a first aperture configured to allow access to a bur receptacle of the dental hand piece;

a second aperture adjacent the first aperture, said second aperture configured for routing of air and water provided by the dental hand piece for application to a patient in an operating field of a bur positioned in the bur receptacle; and a protective device configured to cover said second aperture when the dental hand piece is not in use.

10. A cover according to claim 9 wherein said protective device is spring loaded.

11. A cover according to claim 9 further comprising a filter, said filter configured to fit within said aperture.

12. A cover according to claim 11 wherein said filter is impregnated with an anti-biological contamination agent.

13. A cover according to claim 11 wherein said filter is configured to filter air and water provided by the dental hand piece and routed through said second aperture for application to a patient.

14. A dental system comprising:

a hand piece having a housing and including a bur and air and water outlets for performing dental operations in an oral operating field;

an inner cover separate from said housing of said hand piece having a shape substantially conforming to a shape of said hand piece for enclosing said hand piece and including a first aperture for receiving said bur, a second aperture for passing air and water from said air and water outlets of said hand piece and a third aperture for dissipation of compressed air used to drive an air turbine head; and an outer cover having a shape substantially conforming to a shape of said inner cover for enclosing said inner cover and including a first aperture for receiving said bur, a second aperture for passing air and water passed from said inner cover to said operating field and a third aperture for dissipation of compressed air to drive an air turbine head.

15. A dental system according to claim 14 wherein said third aperture includes a soft insert for damping vibration and noise.

16. A dental system according to claim 15 wherein said soft insert is comprised of a rubber material.

17. A dental system according to 14 wherein said third aperture dissipates said compressed air away from a patient's mouth.

* * * * *